(12) United States Patent
Stephenson et al.

(10) Patent No.: US 7,827,855 B2
(45) Date of Patent: Nov. 9, 2010

(54) METHOD AND KIT FOR ADSORBENT PERFORMANCE EVALUATION

(75) Inventors: Neil Andrew Stephenson, E. Amherst, NY (US); Philip Alexander Barrett, Tonawanda, NY (US); Steven J. Pontonio, Eden, NY (US); Michael T. Freiert, Tonawanda, NY (US); Jesus Gallego-Preciado Nieto, Grand Island, NY (US)

(73) Assignee: Praxair Technology, Inc., Danbury, CT (US)

( * ) Notice: Subject to any disclaimer, the term of this patent is extended or adjusted under 35 U.S.C. 154(b) by 198 days.

(21) Appl. No.: 12/274,646

(22) Filed: Nov. 20, 2008

(65) Prior Publication Data

US 2010/0000306 A1     Jan. 7, 2010

Related U.S. Application Data

(63) Continuation-in-part of application No. 12/166,061, filed on Jul. 1, 2008.

(51) Int. Cl.
*G01N 5/00* (2006.01)

(52) U.S. Cl. .................. 73/73; 96/417; 96/422

(58) Field of Classification Search ........... 73/73; 96/108–154, 228, 417, 422
See application file for complete search history.

(56) References Cited

U.S. PATENT DOCUMENTS

| 3,756,782 | A |   | 9/1973 | Phillips |
| 4,214,011 | A | * | 7/1980 | Strube .................. 426/591 |
| 4,237,726 | A |   | 12/1980 | Peterson et al. |
| 4,597,778 | A | * | 7/1986 | Szonntagh ............... 95/26 |
| 4,744,221 | A | * | 5/1988 | Knollmueller ........... 62/46.1 |
| 5,013,335 | A | * | 5/1991 | Marcus ................... 95/128 |
| 5,069,887 | A | * | 12/1991 | Suenaga et al. .......... 95/128 |
| 5,112,590 | A | * | 5/1992 | Krishnamurthy et al. . 423/418.2 |
| 6,772,536 | B2 | * | 8/2004 | Ely et al. .................. 34/380 |
| 2004/0069144 | A1 | * | 4/2004 | Wegeng et al. ........... 95/106 |
| 2006/0245994 | A1 | * | 11/2006 | Watanabe et al. ........ 423/305 |
| 2007/0004591 | A1 | * | 1/2007 | Itabashi et al. .......... 502/414 |

FOREIGN PATENT DOCUMENTS

| EP | 0 484 121 A1 | 5/1992 |
| FR | 2 652 899 | 4/1991 |
| JP | 3110444 | 5/1991 |

* cited by examiner

*Primary Examiner*—David A. Rogers
(74) *Attorney, Agent, or Firm*—Salvatore P. Pace

(57) ABSTRACT

The present invention generally relates to methods and kits for measuring and analyzing degradation of adsorbent materials, particularly for adsorbent materials used in gas separation processes. The present invention can assess the damage to adsorbent due to contamination including moisture contamination and it can assess damage that is not contaminant-related. The advantage to the present invention is that it can detect degradation of adsorbent directly at the plant site before the degradation affects production. Another advantage is that it can conclusively determine whether the adsorbent is damaged. Because it is so inexpensive to run, the test of the present invention can be conducted to determine adsorbent damage and to confirm whether the damage continues to be an issue. The present invention can test adsorbents in any form, including, but not limited to, bead, pellet or powder form.

18 Claims, 3 Drawing Sheets

METHOD AND KIT FOR ADSORBENT PERFORMANCE EVALUATION

CROSS REFERENCE TO RELATED APPLICATIONS

The present application is a continuation-in-part application to U.S. patent application Ser. No. 12/166,061 filed on Jul. 1, 2008, the disclosure of which is incorporated by reference herein.

FIELD OF THE INVENTION

The present invention generally relates to methods and kits for measuring and analyzing degradation of adsorbent materials, particularly for adsorbent materials used in gas separation processes.

BACKGROUND OF THE INVENTION

Gas separation is accomplished by processes such as pressure swing adsorption (PSA), vacuum pressure swing adsorption (VPSA), and temperature swing adsorption (TSA). These processes use vessels or beds containing one or more layers of adsorbent materials that adsorb one or more unwanted gases and produce the desired product gas. During the process cycle, the adsorbent materials adsorb the unwanted gases and then are regenerated by the removal of the unwanted gases by pressure, vacuum or temperature swings. Typical adsorbents used in these processes include zeolites, alumina and silica and combinations thereof.

Repeated use of an adsorbent causes degradation and eventually renders the adsorbent materials ineffective, such that the adsorbent materials need to be replaced periodically. Degradation of the adsorbent results in plant capacity decline and plant inefficiency, which is costly and time consuming. Often, adsorbent degradation is not detected until the product quality and/or overall plant performance is affected.

Currently, the testing of adsorbents is done by taking samples of the used adsorbent and subjecting them to various performance tests (including capacity measurements) and/or spectroscopic studies that are generally best performed in a laboratory or by a third party off-site. These methods of testing are slow and costly. It would be desirable to have a method of testing adsorbent degradation and quality that is quick and accurate and able to be conducted on-site at the separation plant.

The test methods currently in use include a Karl Fischer titration (KF) that determines trace amounts of water using potentiometric or coulometric titration. The application of KF methods to adsorbents such as zeolites requires system modifications whereby the sample is heated to high temperatures (about 1000° C.) and the water released is swept using a purge gas through a conventional KF cell. KF methods can specifically test for water content, unlike other loss on ignition (LOI) thermal methods that detect the loss of any volatile substance. However, the KF methods require the use of equipment that is very costly and not conducive to conducting the analysis outside of a laboratory, nor can they test for any other type of damage other than moisture damage.

LOI methods are based on the change in mass as a result of heating a sample under specified conditions. The LOI is expressed as a weight percentage of the dry mass. For example, a sample is heated in a furnace to a high temperature (e.g., 1000° C.) and the difference in mass before and after the ignition process is used to calculate the LOI. The LOI test measures the release of all volatiles which are adsorbed by the sample and cannot specifically test for degradation due to contamination by a specific contaminant or assess sample performance.

A near-infrared (NIR) moisture analyzer (e.g., Model #KJT-100, Kett US, Villa Park, Calif., USA) measures moisture levels based on the principle that water absorbs certain wavelengths of light. An optical filter is used to select a wavelength that is either moisture specific (e.g., 1200, 1450 and 1950 nm) or not moisture specific (e.g., 1300 nm). This non-specific wavelength serves as a reference and incident radiation is reflected off a sample and measured by a lead sulfide (PbS) detector. The ratio of absorbed light to reference light is proportional to moisture content in the sample. Similar to KF titration, the NIR moisture analyzer only detects water and will not detect any other types of damage to the adsorbent and is very expensive.

An electronic moisture balance (e.g., Model #EB-340MOC, Shimadzu Corporation, Columbia, Md., USA) determines moisture content in solid substances using a thermogravimetric method. Far-infrared radiation is applied to the surface of a sample to heat it, then the sample is weighed upon drying and compared to the original weight. For many adsorbents such as zeolites, the output of the infrared heaters in commercial moisture balances is insufficient to remove all of the adsorbed water. Furthermore, the moisture balance can only detect moisture content and is very expensive.

Japanese Patent No. JP3110444 describes a method for measuring the adsorption performance of a solid adsorbent wherein a measuring gas containing the adsorption component is introduced into a vessel filled with the solid adsorbent. The measuring gas exits the vessel and goes through an analyzer that analyzes the amount of the adsorption component adsorbed by the solid material.

U.S. Pat. No. 4,237,726 (Peterson et al.) describes a process for predicting the useful life of a respirator cartridge wherein the process measures the weight increase of a sorptive agent when exposed to a gas mixture of dry air and a preselected organic vapor. In this process, the breakthrough time of the cartridge is determined by using the measured breakthrough time of the preselected vapor.

Most of the prior art also involves the use of cumbersome equipment that cannot be used on-site at a plant and the methods are time consuming, expensive and inefficient. The prior art processes do not determine the source of damage to the sorptive agent (e.g., contamination or other performance degradation), have long turnaround times and/or are not readily carried out in a field location or easily compiled in a kit form. Results of the currently used methods are frequently received after the plant adsorbents have been irreversibly damaged, resulting in an expensive reload of the adsorbent beds. A method is needed that can provide diagnostic results quickly, identify the cause of plant degradation at an early stage and allow plant engineers to perform effective preventative maintenance procedures to ensure the integrity of the adsorbent materials.

BRIEF SUMMARY OF THE INVENTION

The present invention is directed to a method of detecting and evaluating performance degradation of an adsorbent on-site at a gas separation plant.

The present invention can assess the damage to adsorbent due to contamination and it can assess damage that is not contaminant-related. The advantage to the present invention is that it can detect degradation of adsorbent before the degradation affects production. Another advantage is that it can conclusively determine whether the adsorbent is damaged.

Because it is so inexpensive to run, the test of the present invention can be conducted to determine adsorbent damage as part of routine plant maintenance and to confirm whether the damage continues to be an issue. The present invention can test adsorbents in any form, including, but not limited to, bead, pellet or powder form.

One embodiment of the present invention is a method of determining gas capacity of an adsorbent material used in a gas separation process comprising the steps of:

(a) taking a sample of the adsorbent material used in the gas separation process and placing the sample in a container means in a controlled environment, wherein the controlled environment is purged by flowing a dry gas;

(b) adsorbing the dry gas onto the sample of adsorbent material;

(c) weighing or measuring the volume of the sample of the adsorbent material in the controlled environment;

(d) optionally measuring the ambient temperature of the controlled environment;

(e) saturating the sample with a displacing agent and displacing the adsorbed gas from the sample of adsorbent material;

(f) measuring the volume of gas released from the sample of adsorbent material; and (g) calculating the ratio of gas released to the weight of the sample and comparing the result with values determined for the same adsorbent material which is deemed to meet the performance requirements of the application (i.e. well manufactured, pristine sample).

Another embodiment of the present invention is a kit for practicing the method of the present invention, comprising:

(a) a test cell or means for measuring gas volume or pressure;

(b) an atmosphere control system;

(c) a weight-measuring means or a volume-measuring means;

(d) at least one sample transfer means with an airtight lid;

(e) at least one sample-containing means with an airtight septa cap;

(f) a displacing agent and displacing agent containing means;

(g) a gas flow measuring and controlling device;

(h) at least one cannula; and (i) a temperature measuring means.

BRIEF DESCRIPTION OF THE DRAWINGS

For a more complete understanding of the present invention and the advantages thereof, reference should be made to the following Detailed Description taken in conjunction with the accompanying drawings in which.

DETAILED DESCRIPTION OF THE INVENTION

Figure 1:
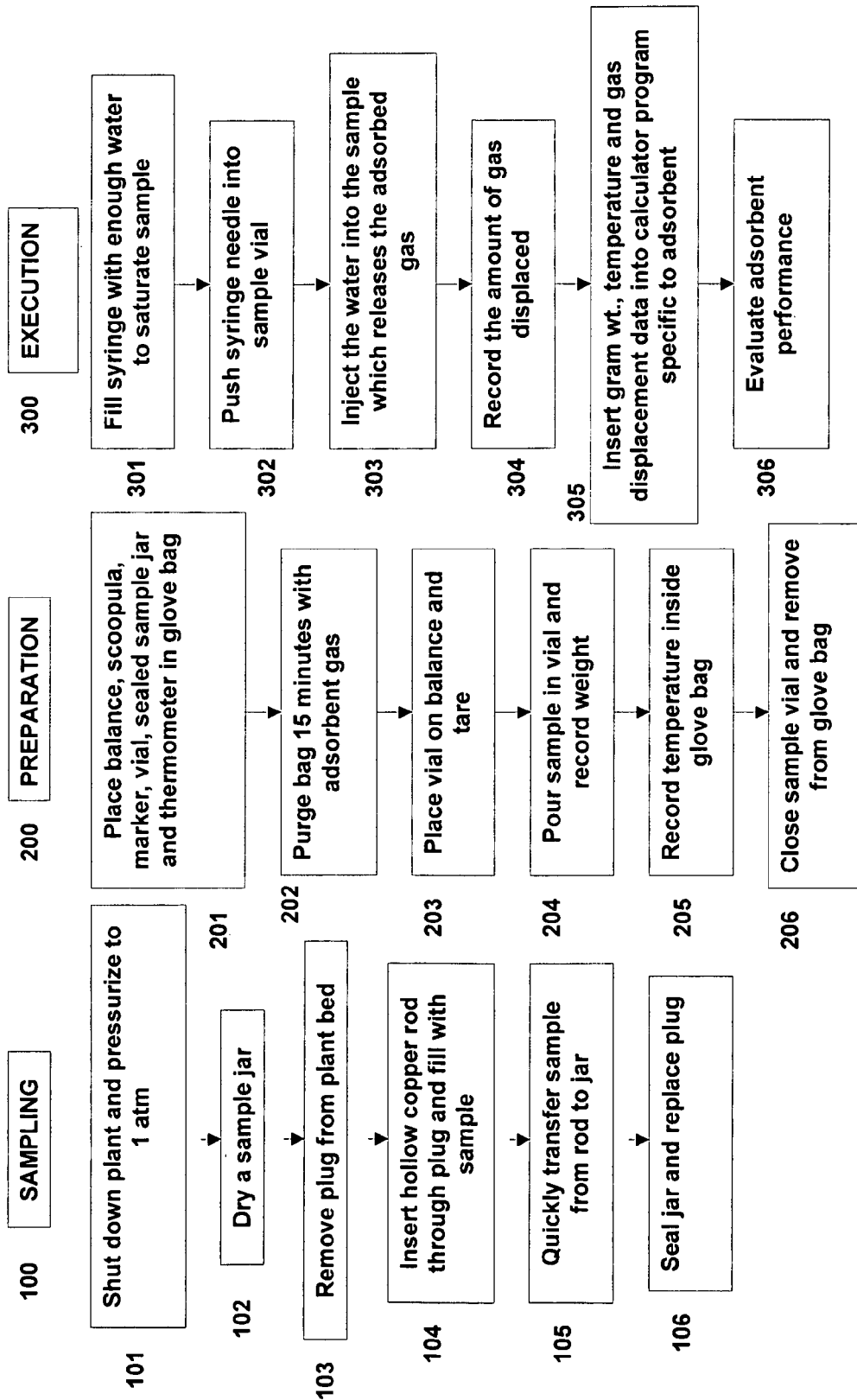
FIG. 1 is a schematic illustrating a workflow diagram for the test method of the present invention.

The present invention is a method of detecting and evaluating performance degradation of an adsorbent on-site at a gas separation plant by determining the gas capacity of the adsorbent, said method comprising the steps of:

(a) obtaining at least one representative sample of adsorbent from adsorbent vessels in a gas separation plant;

(b) placing said sample in a controlled atmosphere, such as a secondary atmosphere control device;

(c) saturating said sample with a test gas in the controlled atmosphere;

(d) weighing said sample in the controlled atmosphere;

(e) measuring the ambient temperature in the controlled atmosphere;

(f) desorbing the test gas from the sample;

(g) measuring the amount of test gas desorbed from the sample; and (h) comparing measurements obtained for sample with measurements for an ideal adsorbent material at the same ambient temperature.

In this specification, the terms "adsorbent" and "adsorbent material" may be used interchangeably to mean the adsorbent material used in a gas separation process. The terms "adsorbent vessel" and "adsorbent bed" may be used interchangeably to mean the vessels in a gas separation plant packed with adsorbent material. The term "ideal" as used herein to describe adsorbent material means adsorbent material that is the same type of material as the adsorbent sample, but that has not yet been used and meets the performance standards for the particular application. The term "fully activated" as used to describe adsorbent material means that the adsorbent material meets the performance standards for the particular application. One way that this can be quantified is by measurement of water content by the Karl Fischer method (e.g., zeolites have a residual water content of less than 0.15 wt %; alumina has a residual water content of 3-10 wt %; and silica has a residual water content of 3-10 wt %) or any other suitable moisture test. The term "syringe" as used herein means a simple piston pump consisting of a plunger that fits tightly in a tube. The plunger can be pulled and pushed along inside a cylindrical tube (the barrel), allowing the syringe to take in and expel a liquid or gas through an orifice at the open end of the tube. The open end of the syringe may be fitted with a hypodermic needle, cannula, nozzle, or tubing to help direct the flow into and out of the barrel. In this specification, the term "cannula" is used interchangeably with "needle" to describe a tube which can be inserted through a barrier (such as a septa cap) for the delivery or removal of a liquid or gas. The term "secondary atmosphere control device" as used herein means a device or system having a controlled atmosphere, within which the method of this invention can be performed. The secondary atmosphere control device can be an atmosphere control system such as a Glove Bag™ or glove chamber (where the term "glove chamber" is a Glove Bag™ like substitute e.g., a PVC bag with cut outs allowing for insertion of the tester's hands).

Another embodiment of the present invention is a field test kit for use in evaluating performance degradation of an adsorbent comprising the following:

One (1) atmosphere control system (e.g., Glove Bag™, Glas-Col, LLC, Terre Haute, Ind., USA or glove chamber)

One (1) balance with readability of 0.01 g (e.g., Blade V2-50, American Weigh Scales, Inc., Charleston, S.C., USA)

At least one (1) vial with airtight septa cap, capable of holding up to 2 g of adsorbent One (1) test cell (e.g., a glass syringe with free moving plunger up to 60 ml displacement, such as a 50 ml syringe, catalog #14-825-11A, from Fisher HealthCare, Houston, Tex., USA)

One (1) gas flow measuring and control device (e.g., a rotameter);

One (1) valve means for gas supply shut-off (e.g., ¼ inch ball valve);

One (1) scoopula or other device for sample transfer;

At least one (1) sample jar with airtight lid used to transfer adsorbent sample from vessel;

One (1) marker pen or other instrument for sample labeling;

One (1) or two (2) extra cannulae; and

One (1) temperature measuring means, (e.g. a thermometer).

Optionally, one (1) pair of gloves for use with atmosphere control system;

Optionally, one (1) sealable container containing suitable displacing agent, such as water;

Optionally, one (1) sealing device (depending on atmosphere control system);

The airtight septa caps and lids for the vials and sample jars should form an airtight seal and can be made of materials such as rubber or Teflon®. The sealable container containing water should be spill-proof and keep the water inside. The container should be big enough to hold enough water to test at least three samples (e.g., at least 12 ml). Furthermore, in order to place items such as the balance into the atmosphere control system, a large opening is needed to insert the items. The sealing device is used to close up the opening to obtain a controlled atmosphere. Examples of acceptable sealing devices include, but are not limited to, a zip-lock closure, a zipper, or binder clips.

One embodiment of the present invention is a method of evaluating the performance degradation of an adsorbent on-site at a separation plant, wherein the method comprises a sampling stage, a test preparation stage and a test execution stage. FIG. 1 shows a flow chart consistent with implementing this embodiment of the present invention.

Stage 1: Sampling (100)

A sample of at least 1 g (preferably, at least 10 g) of adsorbent is first taken from an adsorbent vessel in a gas separation plant. It is critical that the sample is transferred from the vessel to a sample container with minimal if any exposure to the outside atmosphere. Adsorbents can be extremely hydrophilic and even accidental or unnecessary exposure to air can allow moisture to be adsorbed onto the sample. In order to achieve the most accurate test result, the sample must stay in the same condition during transfer as it was when sampled. Any moisture adsorbed during the transfer can affect the accuracy of the test. For example, for a VPSA plant using nitrogen-selective LiX adsorbent, an acceptable method for removing a sample from a VPSA adsorbent bed is as follows:

(a) Shut down the plant and pressurize the adsorbent bed to 1 atmosphere (101);

(b) Dry the sample jar by using a heat gun or by adding dry zeolite to the jar and then emptying the jar (102);

(c) Remove the plug from the adsorbent bed access point (i.e., thermocouple port or other suitable point of ingress) and cover immediately with duct tape or other sealing agent (103);

(d) Remove the duct tape and immediately push a thin-walled copper pipe into the center of the bed, then pull the pipe (filled with adsorbent material) from the bed and replace duct tape (104);

(e) Pour the adsorbent sample in the pipe into a dry sample jar (105); and (f) Secure an airtight lid onto the sample jar, remove the duct tape from the adsorbent bed and replace the plug (106).

It is important to take the adsorbent sample from the interior of the adsorbent bed to have a representative sample. The adsorbent material near the sampling port may be wetter than the majority of the adsorbent material in the bed. The sampling and sample handling procedure described herein is one example of an appropriate procedure. Any procedure that can maintain the integrity of the sample is appropriate for the present invention.

Stage 2: Test Preparation (200)

Prepare a source of a dry gas to be used as the test gas (e.g., $N_2$, $O_2$, air, $CO_2$). The test gas should be one that is readily available in dry form and that will be appreciably adsorbed by the adsorbent. Place the balance, scoopula, marker, vials, thermometer and sealed sample jars containing adsorbent samples obtained in Stage 1 in the atmosphere control system (201), then purge the system for at least 15 minutes with a dry gas (202). Place an uncapped vial on the balance and tare it (203). Place a suitable quantity of the adsorbent sample into the vial (i.e. a suitable quantity is that which when in pristine condition will release a volume of gas which is measurable by the test cell and preferably in the range 65-85% of its full scale), and record the precise weight of the sample (204). The sample will have adsorbed the dry test gas that was purged through the atmosphere control system. The sample must be big enough to provide significant results. A sample that is too small will have a margin of error that is too large and there will not be sufficient adsorption and displacement of the test gas. If the sample is too large, then the test cell will not be big enough to hold the gas. The ideal sample amount can be determined from the expected capacity for the test gas of adsorbents of the same type in pristine condition (i.e. those which meet the performance requirements of the application or specification), in combination with the volume of the test cell. For example, if the expected capacity for the adsorbent is 25 ml/g and the test cell has a volume of 50 ml, then a sample in the range of 1.3 to 1.7 g is preferable. Record the temperature inside the atmosphere control system (205). Close the sample vial using a septa cap and remove the vial from the atmosphere control system (206).

Stage 3: Execution (300)

Figure 2:
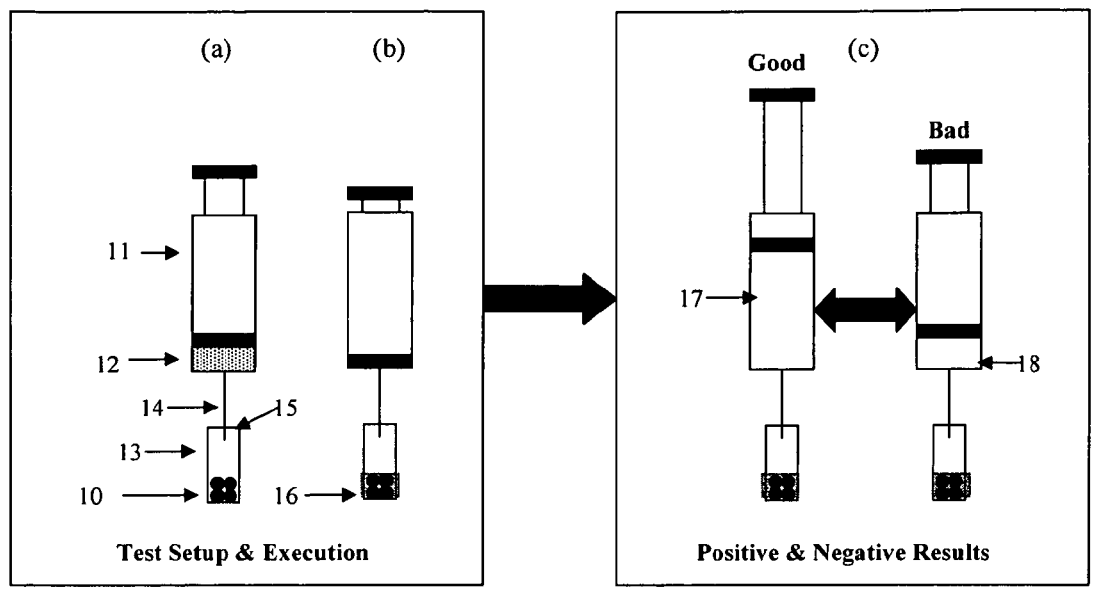
FIGS. 2(a) and 2(b) are schematics illustrating the test set-up and execution stages of the present invention, respectively.
FIG. 2(c) is a schematic illustrating good and bad test results obtained by using the present invention.

FIGS. 2(a) and 2(b) are graphical illustrations of the test set-up and execution stages, respectively, of the present invention. To displace the adsorbed test gas from the adsorbent sample (10), saturate the sample with a displacing agent, e.g., water. Attach a cannula (14) to the test cell (depicted in FIG. 2 as a syringe (11)) and fill it with enough water (12) to fully saturate the sample (301). For a sample of approximately 1.3 to 1.7 g, about 4 ml of water will be sufficient to saturate it. Insert the cannula into the sample vial (13) through the septa cap (15) (302) and inject the water into the sample vial (303). The water saturates the sample (16) and desorbs the test gas from the sample and the test gas is released from the sample back up through the cannula and collected in the syringe. FIG. 2(c) illustrates positive and negative results of the test. If a lot of test gas is released, the syringe will be filled (17), indicating that the adsorbent capacity is good. If very little test gas is released and the syringe is relatively empty (18), then the adsorbent capacity is bad. Although any appropriate apparatus that can contain and measure the test gas volume may be used as the test cell, the use of a glass syringe with water as the displacing agent is particularly effective because the water serves as a seal between the syringe barrel and the syringe plunger, making the syringe gas tight.

Figure 3:
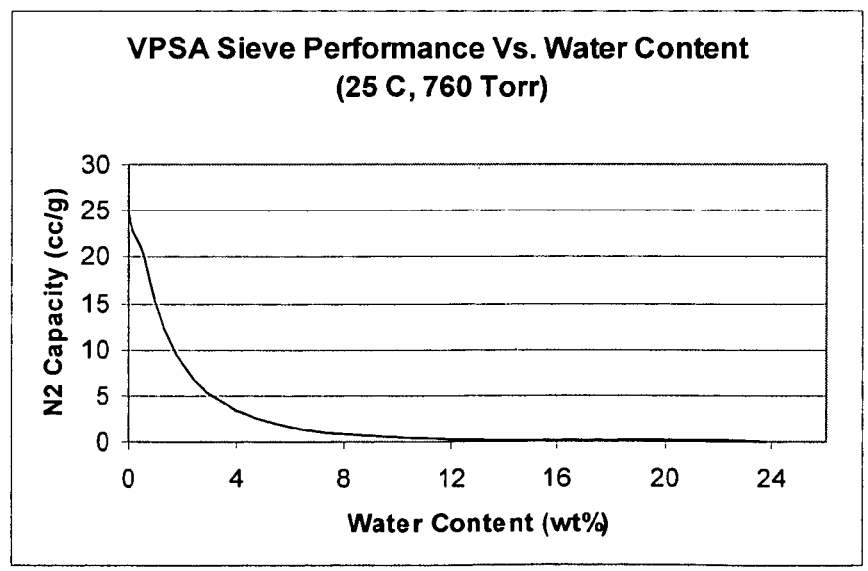
FIG. 3 is a graphical representation of the effect of water content on LiX2.0 performance.

The total volume of test gas collected in the syringe is recorded and noted (304). Each adsorbent type in its fully activated and ideal state will adsorb a known amount of a certain gas. For example, a sample of highly exchanged (i.e., greater than 96%) lithium-exchanged zeolite X having a $SiO_2/Al_2O_3$ ratio of 2 (LiX2.0) in beaded form adsorbs 24 ml of nitrogen per gram of sample when in its ideal state. Water contamination is one reason for degradation of LiX2.0 adsorbent performance in VPSA applications. For a given adsorbent, test gas and measurement temperature, a curve of performance versus % contaminant can be generated (see, e.g., FIG. 3). The displaced test gas volume per gram of sample is calculated from the measurements taken (i.e., displaced test gas volume (ml)/sample weight (g)). The calculated value for a specific temperature can be compared to a pre-generated curve such as that in FIG. 3 and the extent of contamination can be determined (305, 306). FIG. 3 illustrates the effect of water contamination on the adsorption capacity of LiX2.0 at a temperature of 25° C. The curve can be established experimentally for each adsorbent material for different temperatures by exposing the adsorbent to moisture and plotting the field test result (ml/g test gas capacity) versus Karl Fischer residual water test result or other suitable moisture specific test such as NIR moisture meter. For the purpose of this invention, one may also use a performance curve obtained from adsorbent material manufacturers, textbooks or other references.

EXAMPLE 1

Field Test of Adsorbent Performance at VPSA Plant 1

A VPSA axial system, designated Plant 1, was not performing at normal capacity, possibly due to degradation of the zeolite adsorbent in the beds. The field test kit of the present invention was sent to Plant 1 to perform an on-site test to determine if there was any adsorbent degradation and whether the adsorbent degradation was the cause of the loss of plant capacity. Plant 1 contained two beds, A and B. Each bed was comprised of two different adsorbents, Adsorbent 1 and Adsorbent 2. Both adsorbents were lithium-exchanged type X zeolites. Adsorbent 1 had a $SiO_2/Al_2O_3$ ratio of 2 (LiX2.0) and Adsorbent 2 had $SiO_2/Al_2O_3$ ratio of 2.3 (LiX2.3). Adsorbent 2 was at the top of each bed and Adsorbent 1 was at the bottom of each bed.

Figure 4:
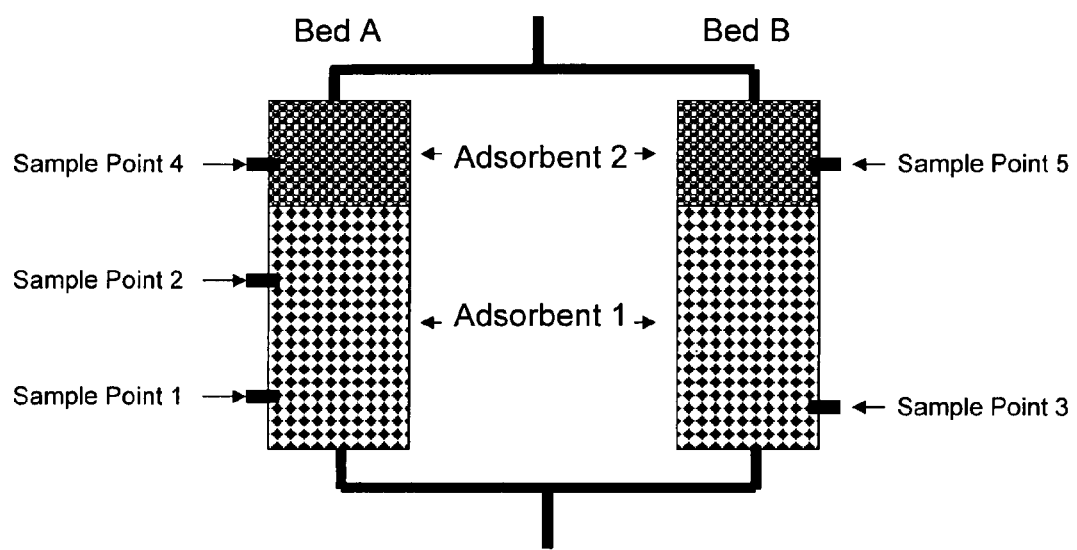
FIG. 4 is a schematic illustrating sampling points in two adsorbent beds.

The sampling and test procedures were as follows:

1. A total of five (5) samples were taken from the two beds. FIG. 4 shows the sample points where each of the samples was taken. Bed A was sampled at the top, middle and bottom (three locations; Sample Points 4, 2 and 1, respectively) and Bed B was sampled at the top and bottom (two locations; Sample Points 5 and 3, respectively). It is important to sample several locations in a bed because different locations in the bed may experience different amounts of adsorbent damage or contamination. The samples were handled in accordance with the method described herein, such that no additional contamination occurred during removal from the bed.

2. A dry nitrogen source was connected to a secondary atmosphere control device, such as an inflatable polyethylene glove chamber using plastic tubing. For this experiment, a Glove Bag™ (Glas-Col, LLC), was used as the secondary atmosphere control device. A rotameter was connected to the plastic tubing to control the nitrogen flow.

3. The samples obtained from the bed were placed in the glove chamber, together with the balance, vials, scoopula and a marker pen.

4. The glove chamber front opening was sealed using clips and the dry nitrogen was purged through at 4 slpm for 15 minutes.

5. A vial without a cap was placed on the balance and tared. Using the scoopula, approximately 1.5 g of a sample was poured into the vial and the exact weight and sample identification number were recorded. After weighing and labeling the vial is sealed using the septa cap.

6. Step 5 was repeated for all of the other four samples.

7. The sealed vials containing the samples were removed from the glove chamber.

8. Four ml of water was aspirated into a 50 ml capacity glass syringe.

9. The syringe cannula was pushed through the septa cap of a sample vial and the water was injected into the sample, allowing the displaced gas to be transferred into the syringe. The amount of displaced gas transferred into the syringe was recorded. It should be noted that the release of gas upon water addition is extremely rapid and that significant pushback occurs during the injection. However, it is not critical that all of the water is injected in a single continuous step. The same results are obtained whether water is added in pulses or in one continuous injection.

10. Steps 8 and 9 were repeated for all of the other four samples.

The data for Example 1 are listed in Table 1 where it was assumed that the temperature during the test was around 27° C. and the pressure was atmospheric.

TABLE 1

Water Detection Test Calculator; Test Gas: Nitrogen

| | Adsorbent Type | | | | |
|---|---|---|---|---|---|
| | Adsorbent 1 | | | Adsorbent 2 | |
| Sample | #1 | #2 | #3 | #4 | #5 |
| Bed | Bed A | Bed A | Bed B | Bed A | Bed B |
| Sample Point | Bottom T/C | Middle T/C | Bottom T/C | Top T/C | Top T/C |
| Weight of adsorbent sample (g) | 1.50 | 1.71 | 1.50 | 1.46 | 1.54 |
| Water added to syringe (ml) | 4 | 4 | 4 | 4 | 4 |
| Syringe reading after water injection (ml) | 32 | 35 | 26 | 12 | 20 |

TABLE 1-continued

Water Detection Test Calculator; Test Gas: Nitrogen

| | Adsorbent Type | | | | |
|---|---|---|---|---|---|
| | Adsorbent 1 | | | Adsorbent 2 | |
| Sample | #1 | #2 | #3 | #4 | #5 |
| [1]Calculated $N_2$ displaced per gram adsorbent (ml) | 18.67 | 18.71 | 14.67 | 5.48 | 10.39 |
| [2]Calculated water in adsorbent (wt %) | 0.69 | 0.69 | 1.35 | 3.79 | 2.88 |

[1]Calculated as follows: (Syringe reading after water injection - Water added to syringe)/Weight of adsorbent sample
[2]Uses the "Calculated $N_2$ displaced per gram adsorbent" and the calculated curve for the degradation of N2 capacity for the specific adsorbent.

The results showed that the top of each bed had become partially deactivated by adsorbing moisture. Generally, a reading above approximately 0.8 wt % will have a significant impact on the adsorbent performance. It was determined that the top of the beds were contaminated and the appropriate measures were taken to replace the contaminated adsorbent and optimize plant performance. It should be noted that the temperature in the glove chamber was not measured for this experiment. However, it has been determined that the accuracy of the test can be improved still further by measuring the test temperature and accounting for the effect of this in the data analysis (i.e., using or deriving a curve at or close to (±2° C.) the test temperature). Therefore, temperature should be recorded and entered into the equation to be factored into the water content calculation.

FIGS. 5a and 5b are graphical representations of the degradation of nitrogen capacity for Adsorbent 1 and Adsorbent 2, respectively, as the water content increases, measured at a pressure of 1 atm and a temperature of 27° C.

EXAMPLE 2

Determination of Adsorbent Damage During Manufacturing

One embodiment of the present invention can test for adsorbent damage not related to contamination. A sample of NaX zeolite powder in a hydrated state (LOI of at least 20 wt %) having a $SiO_2/Al_2O_3$ ratio of 2.0 was suspected of being damaged. The sample was tested according to the following method:

1. A glass test tube (open only at one end), equipped with a septa cap at the opening and two syringe needles, each possessing an on/off valve, were each weighed separately and the weights were recorded.

2. A sample of approximately 0.5 g was placed in the test tube and the test tube was sealed with the septa cap. The sample weight was selected in accordance with expectations for the adsorption capacity of the sample and considering the volume measurement limits of the syringe. The sample must be sufficient to obtain significant adsorption and desorption of a test gas. This particular zeolite can adsorb 105 ml/g $CO_2$ at 27° C. and 1 atm when fully activated and in its ideal state. If a 50 ml syringe is used, the sample size should be at 0.3 g, and preferably between 0.3 and 0.4 g. This will ensure that the gas release from the sample is large enough to be accurate but small enough to stay within the syringe volume limit.

3. The septa cap was then punctured with the two previously weighed needles. One of the needles was attached to a tube connected to a source of dry nitrogen and the other needle was left open to the atmosphere.

4. A flow of nitrogen was sent through the tube and into the test tube.

5. The sample was heated by ramping up to 400° C. gradually over the course of 1 hour and left at 400° C. for 30 minutes using a heating mantle equipped with a temperature controller. This activated the sample by driving out the water. It should be noted that a small layer of sample was used to allow for a more rapid activation without the concern of steaming, which could damage the zeolite.

6. The sample was then cooled to room temperature, the flow of nitrogen was stopped, and the needles closed off to avoid contamination by moisture in the ambient air.

7. The test tube, adsorbent, septa cap and needles were weighed and the initial weight of these equipment was subtracted to determine the activated sample weight.

8. The sealed test tube containing the test sample was then connected through one of the needles to a dry $CO_2$ supply, with the other needle being left open to the atmosphere.

9. A flow of $CO_2$ was sent through the test tube and the $CO_2$ was adsorbed onto the sample. $CO_2$ is used because more volume is adsorbed so that despite the smaller sample size, a reasonable amount of gas can be released from the sample by the displacing agent and measured.

10. After allowing the sample to reach equilibrium (by contact with the $CO_2$ for approximately 10 minutes), the flow of $CO_2$ was stopped and the outlet needle was closed off.

11. The inlet needle was detached from the $CO_2$ source and attached to a glass syringe filled with 4 ml of water (used as the displacing agent).

12. The water was injected into the test tube to displace the adsorbed $CO_2$ from the sample and force the displaced $CO_2$ back into the syringe. The displaced $CO_2$ was then measured.

The NaX zeolite sample having a $SiO_2/Al_2O_3$ ratio of 2.0 should adsorb 105 ml/g of $CO_2$ at 27° C. and 1 atm, if it is fully activated and in an ideal state. The activation treatment at 400° C. under dry nitrogen ensures the sample was fully activated with a moisture content of less than 0.1 wt %, therefore any measured displacement below 105 ml/g at a test temperature of 27° C. and 1 atm signals the adsorbent has been damaged, with lower gas displacement signifying greater damage.

These examples demonstrate specific embodiments of the present invention. Another embodiment of the invention comprises a field test method as described herein, further comprising the use of more than one test gas, including but not limited to nitrogen, air or $CO_2$.

In another embodiment of the present invention, the method of measuring the displaced gas is to measure the pressure increase over a fixed volume. The adsorbent sample is contained in a sealed container with water or other displacing agent pumped in to saturate the adsorbent sample. The displaced gas would be released and subsequently increase the pressure inside the fixed volume container. A pressure gauge is used to measure the pressure increase and enable comparison with an ideal adsorbent which is uncontaminated and undamaged tested under the same conditions.

The displacing agent used in the above examples is water, but different displacing agents may also be used. Any agent that provides the displacement of the adsorbed test gas for measurement may be used, such as alcohol or any water-based liquid.

The method and kit of the present invention may be used to test many different types of adsorbent. Any adsorbent for which the ideal or expected capacity of a gas is known or can be measured or calculated can be tested using the method and kit of the present invention.

The method and kit of the present invention may also be used to determine different types of damage to the adsorbent. To test for damage other than contamination by contaminants such as moisture, the method would further comprise activating the adsorbent sample before running the test as described herein. Activation of the adsorbent sample drives contaminants such as moisture from the sample and any performance loss is then attributable to other factors.

The method of the present invention may be modified such that an adsorbent sample could be exposed to moisture during normal use, requiring an activation step. Adsorbents for prepurification units (PPUs) and hydrogen PSAs can be tested using this method. Although other test gases may be used, $CO_2$ is the preferred test gas since the adsorbents typically used in PPUs and hydrogen PSAs have higher $CO_2$ capacities and will provide for better test accuracy.

In yet another embodiment of the present invention, the test method could comprise partial displacement of the test gas instead of full displacement of the test gas. For example, if for some reason the adsorbent sample could not be fully saturated by the displacing agent, a portion of the adsorbent could be saturated. If partial displacement is calculated, then the baseline partial displacement must also be calculated for the uncontaminated and undamaged adsorbent.

Another embodiment of the present invention is a test method wherein the results are expressed on volumetric basis not gravimetric basis and the weighing step is omitted and there is no need for a balance/scale in the field test kit. The test could be performed using the following sequence of steps:

a. taking a sample of the adsorbent materials used in the gas separation process and placing the sample in a container means in a controlled environment purged with a dry gas;

b. adsorbing the gas onto the adsorbent material in the controlled environment;

c. measuring out a fixed volume of adsorbent;

d. measuring the ambient temperature of the controlled environment;

e. saturating the sample with a displacing agent and displacing the adsorbed gas from the sample of adsorbent material; and f. measuring the volume of gas released from the sample of adsorbent material; and calculating the ratio of the volume of gas released to the volume of the sample Another embodiment of the present invention is a method using a gravimetric or volumetric basis, wherein the pressure generated upon displacement of adsorbed gas by the displacing agent is measured. The test could be performed using the following sequence of steps:

a. taking a sample of the adsorbent materials used in the gas separation process and placing the sample in a fixed volume container means in a controlled environment purged with a dry gas;

b. adsorbing the gas onto the adsorbent material in the controlled environment;

c. weighing the sample of adsorbent material in the controlled environment or measuring out a fixed volume of adsorbent in the controlled environment;

d. measuring the ambient temperature of the controlled environment;

e. saturating the sample with a displacing agent and displacing the adsorbed gas from the sample of adsorbent material; and f. measuring the pressure generated by the gas released from the sample of adsorbent material; and calculating the ratio of the pressure of gas released to the mass or volume of the sample or using a suitable relationship to calculate the volume of gas released from the measured pressure change and calculating the ratio of volume of gas released to the mass or volume of the sample.

The components of the field test kit of the present invention may be substituted with other equipment that serve essentially the same purpose and accomplish the same result. For example, the vessel used to measure the displaced gas in the method and kit of the present invention can be any device that is capable of measuring gas volume. Another example is that the balance could be omitted and replaced with a device to measure out a fixed volume of adsorbent. The results would then be expressed as ml of test gas per ml of adsorbent.

Although the invention has been described in detail with reference to certain preferred embodiments, those skilled in the art will recognize that there are other embodiments within the spirit and the scope of the claims.

What is claimed is:

1. A method of determining gas capacity of an adsorbent material used in a gas separation or purification process comprising the steps of:
    (a) taking a sample of the adsorbent material used in the gas separation process and placing the sample in a container means in a controlled environment purged with a dry test gas;
    (b) adsorbing the test gas onto the sample of adsorbent material;
    (c) measuring out a fixed volume of or weighing the sample of the adsorbent material in the controlled environment;
    (d) saturating the sample with a liquid displacing agent and displacing the adsorbed test gas from the sample of adsorbent material;
    (e) measuring the volume of test gas released from the sample of adsorbent material; and
    (f) determining the gas capacity by calculating the ratio of test gas released to the weight or volume of the sample.

2. The method of claim 1, wherein a step of measuring the ambient temperature of the controlled environment follows step c.

3. The method of claim 1, wherein the adsorbent material selected from the group of zeolites, silica and alumina or a combination thereof, and is in the form of beads, pellets or powder.

4. The method of claim 1, wherein the controlled environment is a glove chamber.

5. The method of claim 1, wherein the dry test gas is nitrogen, carbon dioxide, oxygen or air.

6. The method of claim 1, wherein the container means is a vial with an airtight septa cap and the displacing agent is transferred from a syringe via a cannula through the septa cap into the vial and wherein the volume of gas released from the sample flows back through the cannula into the syringe and is measured in the syringe.

7. The method of claim 1, wherein the displacing agent is water.

8. The method of claim 1, wherein the method is performed at atmospheric pressure.

9. The method of claim 1, wherein the gas separation process is a pressure swing adsorption process, vacuum pressure swing adsorption process, or temperature swing adsorption process.

10. A method of determining the gas capacity of an adsorbent material comprising the steps of:
    (a) taking a sample of the adsorbent material;
    (b) loading the sample into a pre-weighed sample tube;
    (c) flowing a first dry test gas through the sample tube, heating the sample and removing any removable species contained in the sample;
    (d) cooling the sample and stopping the flow of the first test gas;
    (e) re-weighing the sample and sample tube to obtain the sample weight;
    (f) flowing a second dry test gas into the sample tube;
    (g) adsorbing the second test gas onto the sample of adsorbent material;
    (h) saturating the sample with a liquid displacing agent and displacing the adsorbed second test gas from the sample of adsorbent material;
    (i) measuring the volume of the second test gas released from the sample of adsorbent material; and
    (j) determining the gas capacity by calculating the ratio of volume of second test gas released to the weight of the sample.

11. The method of claim 10, wherein the adsorbent material selected from the group of zeolites, silica and alumina or a combination thereof, and is in the form of beads, pellets or powder.

12. The method of claim 10, wherein the first dry test gas and second dry test gas are selected from the group consisting of nitrogen, carbon dioxide, oxygen and air, and the first and second test gases may be the same.

13. The method of claim 10, wherein the displacing agent is water.

14. The method of claim 10, wherein the gas separation process is a pressure swing adsorption process, vacuum pressure swing adsorption process, or temperature swing adsorption process.

15. The method of claim 10, wherein the sample tube is quartz glass tube and the heating is temperature is less than 600° C.

16. The method of claim 15, wherein the displacing agent is transferred from a syringe via a cannula through the septa cap into the quartz glass tube and wherein the volume of gas released from the sample flows back through the cannula into the syringe and is measured in the syringe.

17. A method of evaluating degradation of an adsorbent material used in a gas separation or purification process comprising the steps of:
    (a) taking a sample of the adsorbent material used in the gas separation process and placing the sample in a container means in a controlled environment purged with a dry test gas;
    (b) adsorbing the test gas onto the sample of adsorbent material;
    (c) measuring out a fixed volume of or weighing the sample of the adsorbent material in the controlled environment;
    (d) saturating the sample with a liquid displacing agent and displacing the adsorbed test gas from the sample of adsorbent material;
    (e) measuring the volume of test gas released from the sample of adsorbent material;
    (f) calculating the ratio of test gas released to the weight or volume of the sample; and
    (g) determining the gas capacity by comparing the ratio calculated in step f to a pre-generated performance curve for the adsorbent material.

18. A method of evaluating degradation of an adsorbent material used in a gas separation or purification process comprising the steps of:
    (a) taking a sample of the adsorbent material;
    (b) loading the sample into a pre-weighed sample tube;
    (c) flowing a first dry test gas through the sample tube, heating the sample and removing any removable species contained in the sample;
    (d) cooling the sample and stopping the flow of the first test gas;
    (e) re-weighing the sample and sample tube to obtain the sample weight;
    (f) flowing a second dry test gas into the sample tube;
    (g) adsorbing the second test gas onto the sample of adsorbent material;
    (h) saturating the sample with a liquid displacing agent and displacing the adsorbed second test gas from the sample of adsorbent material;
    (i) measuring the volume of the second test gas released from the sample of adsorbent material;
    (j) calculating the ratio of volume of second test gas released to the weight of the sample; and
    (k) determining the gas capacity by comparing the ratio calculated in step j to a pre-generated performance curve for the adsorbent material.

\* \* \* \* \*